(12) United States Patent
Mildner et al.

(10) Patent No.: US 9,993,275 B2
(45) Date of Patent: Jun. 12, 2018

(54) SURGICAL LOCKING SCREW

(71) Applicant: ZIMMER GMBH, Winterthur (CH)

(72) Inventors: Alexander Mildner, Vienna (AT);
Vladko Kotuljac, Schoemberg (DE)

(73) Assignee: Zimmer GmbH, Winterthur (CH)

( * ) Notice: Subject to any disclaimer, the term of this patent is extended or adjusted under 35 U.S.C. 154(b) by 308 days.

(21) Appl. No.: 14/776,011

(22) PCT Filed: Mar. 17, 2014

(86) PCT No.: PCT/EP2014/055256
§ 371 (c)(1),
(2) Date: Sep. 14, 2015

(87) PCT Pub. No.: WO2014/140360
PCT Pub. Date: Sep. 18, 2014

(65) Prior Publication Data
US 2016/0030097 A1 Feb. 4, 2016

(30) Foreign Application Priority Data

Mar. 15, 2013 (DE) .................... 20 2013 101 135 U

(51) Int. Cl.
*A61B 17/86* (2006.01)
(52) U.S. Cl.
CPC ........ *A61B 17/863* (2013.01); *A61B 17/8605* (2013.01); *A61B 17/864* (2013.01); *A61B 17/8635* (2013.01); *A61B 17/8645* (2013.01)
(58) Field of Classification Search
CPC . A61B 17/864; A61B 17/863; A61B 17/8605; A61B 17/8645
See application file for complete search history.

(56) References Cited

U.S. PATENT DOCUMENTS 5,007,910 A * 4/1991 Anapliotis ........... A61B 17/746
606/65
5,259,398 A * 11/1993 Vrespa ................. A61B 17/863
128/898

(Continued)

FOREIGN PATENT DOCUMENTS

EP 1033111 A1 9/2000
EP 1870050 A2 12/2007

(Continued)

OTHER PUBLICATIONS

"International Application Serial No. PCT/EP2014/055256, International Preliminary Report on Patentability dated Sep. 24, 2015", (W/ English Translation), 14 pgs.

*Primary Examiner* — Christian Sevilla
(74) *Attorney, Agent, or Firm* — Schwegman Lundberg & Woessner, P.A.

(57) ABSTRACT

The invention relates to a surgical locking screw for fastening bone parts in the event of a heel fracture, comprising a front end, a rear driving end having a drive for turning the locking screw, and an external thread, which has a constant thread pitch continuously over the axial extent of the external thread, wherein a major diameter of the external thread is constant in a first axial segment of the locking screw and increases with increasing distance from the front end in a second axial segment adjacent to the first axial segment in the direction of the rear end, wherein a minor diameter of the external thread is constant in the first and second axial segments, wherein the external thread extends, at least approximately, axially continuously over the entire axial extent of the locking screw, and wherein the minor diameter of the external thread extends over the entire axial extent of the external thread.

17 Claims, 2 Drawing Sheets

(56) References Cited

U.S. PATENT DOCUMENTS

Figure 1:
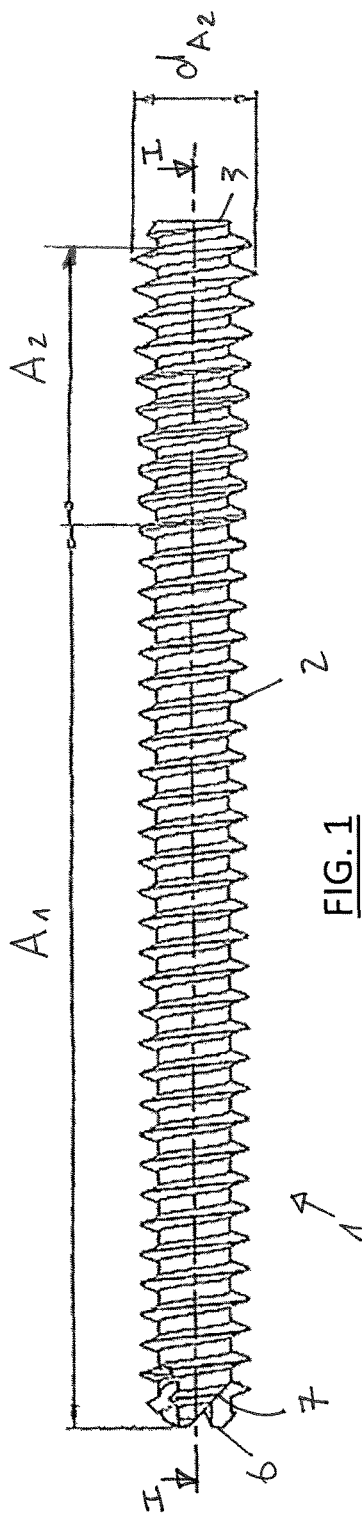

| | | | | |
|---|---|---|---|---|
| D356,868 S | * | 3/1995 | Broberg | D24/156 |
| 5,403,136 A | * | 4/1995 | Mathys | A61B 17/744 411/263 |
| 5,443,509 A | * | 8/1995 | Boucher | A61B 17/861 411/412 |
| 5,601,553 A | * | 2/1997 | Trebing | A61B 17/15 411/399 |
| 5,827,031 A | * | 10/1998 | Swallow | B25B 15/005 411/387.4 |
| 6,030,162 A | * | 2/2000 | Huebner | A61B 17/1682 411/263 |
| 6,565,566 B1 | | 5/2003 | Wagner et al. | |
| 7,582,107 B2 | * | 9/2009 | Trail | A61B 17/863 606/304 |
| 8,029,285 B2 | * | 10/2011 | Holmen | A61C 8/0022 433/174 |
| 8,998,550 B2 | * | 4/2015 | Platt | E05D 1/00 411/386 |
| 2002/0087161 A1 | * | 7/2002 | Randall | A61B 17/683 606/916 |
| 2003/0014054 A1 | | 1/2003 | Huebner | |
| 2003/0028193 A1 | * | 2/2003 | Weil | A61B 17/863 606/304 |
| 2005/0131413 A1 | * | 6/2005 | O'Driscoll | A61B 17/8052 606/286 |
| 2006/0116686 A1 | * | 6/2006 | Crozet | A61B 17/8057 606/281 |
| 2008/0027444 A1 | * | 1/2008 | Malek | A61B 17/686 606/86 A |
| 2009/0312794 A1 | * | 12/2009 | Nason | A61B 17/0401 606/232 |
| 2010/0094352 A1 | | 4/2010 | Iott et al. | |
| 2010/0211118 A1 | * | 8/2010 | Christen | A61B 17/863 606/312 |
| 2011/0060373 A1 | * | 3/2011 | Russell | A61B 17/0401 606/304 |
| 2012/0053639 A1 | * | 3/2012 | Grant | A61B 17/864 606/301 |
| 2012/0083847 A1 | | 4/2012 | Huebner et al. | |
| 2012/0178048 A1 | * | 7/2012 | Cottrell | A61C 8/0025 433/174 |
| 2013/0331947 A1 | | 12/2013 | Surma et al. | |

FOREIGN PATENT DOCUMENTS

| | | |
|---|---|---|
| FR | 2932975 A1 | 1/2010 |
| WO | WO-2012103354 A1 | 8/2012 |
| WO | WO-2014140360 A1 | 9/2014 |

* cited by examiner

SURGICAL LOCKING SCREW

This application is a U.S. National Stage Filing under 35 U.S.C. 371 from International Application No. PCT/EP2014/055256, filed on 2014 Mar. 17 and published as WO2014/140360 A1 on 18 Sep. 2014, which application claims the benefit under 35 U.S.C. 119 to German Application No. 202013101135.5, filed on 2013 Mar. 15; which application and publication are incorporated herein by reference in their entirety.

The invention relates to a surgical locking screw in accordance with the preamble of claim 1 for fixing bone parts in the case of a heel fracture, in particular for fixing bone fractures in the case of a heel fragment fracture. The locking screw consists of a metal material, for example, but can equally consist or comprise a suitable non-metallic material.

To ensure a good healing of heel fractures, it is necessary/sensible to fix the bone pieces relative to one another before the entire foot is put into a cast.

It is the underlying object of the invention to provide suitable locking means or positioning means for this purpose.

This object is satisfied by a surgical locking screw having the features of claim 1.

It is the underlying idea of the invention to provide a locking screw for fixing bone parts in the case of a heel fracture which makes it possible to screw at least one locking screw into the fractured heel such that the locking screw directly contacts or passes through as many bone parts as possible. To allow a rotationally stable fixing of the bone parts, it has proved of value to use two such locking screws which are at least partly spaced apart from one another.

The locking screw described here is characterized in that it has an at least approximately axially throughgoing external thread, i.e. a non-interrupted external thread, which continuously has an invariable thread pitch to prevent a compression of the bone parts. It has surprisingly been found that the healing is hereby substantially improved. In this context, the constant thread pitch relates to a thread turn. That is, with a multi-turn thread, this pitch is given as the spacing of two thread tips of one and the same thread turn.

In order further to minimize the risk of compression, provision is additionally made that a minor diameter of the external thread is constant both in a first, distal axial section to be explained below and in a second axial section behind it, that is proximal, in a screw-in direction, even though the outer diameter of the external thread increases in the second (rear or drive-side) axial section as the spacing from the front end increases, that is from distal to proximal. This construction measure serves to ensure a defined position of the locking screw in the foot despite an omission of compression, and indeed such that an independent advance in the screw-in direction is reliably prevented in that the friction at the end of the screwing in is increased in a cylindrical bore channel due to the increasing external thread diameter in the second axial section. At the same time, an independent release of the screws is prevented by the increased friction of the further outwardly disposed thread tips The locking screw core in contrast has an axially throughgoing cylindrical shape, optionally with the exception of axially front and/or rear chamfers which may optionally be provided.

In other words, the locking screw in accordance with the invention is characterized, despite the omission of different thread pitches and of a diameter increase of the minor diameter of the external thread typical with compression screws, by a locking and abutment function which allows a defined positioning, with the locking and abutment function being realized with an invariable core diameter in this axial section by an external thread diameter increasing in the direction of the screw end and by a friction of the thread in the bone which is thereby increased. An abutment function in the sense used here is not to be understood as a fixed, form-fitting mechanical abutment.

Advantageous embodiments of the invention can be seen from the dependent claims, from the description and from the drawing.

Provision is made in accordance with a further development that the locking screw has an axially throughgoing, central cannulization (central channel) for receiving a Kirschner wire.

The internal diameter of the cannulization is in particular selected from a value range between approximately. 1.0 mm and 3.0 mm and amounts to at least approximately 2.2 mm in an embodiment. The provision in accordance with a further development of a cannulization for a Kirschner wire ensures an optimum, targeted introducibility of the surgical locking screw into the human foot.

In accordance with an embodiment, the external thread can, as explained below, be formed as a self-tapping thread in a front region and/or can open in cutting means of a different design.

Alternatively or additionally, the external thread can furthermore at least regionally have a flank angle which is in particular between 35° and 45° and/or the external thread can be formed as trapezoidal at least regionally.

In the case of the already mentioned provision of an axially throughgoing cannulization, the core section or core region of the crew is hollow cylindrical. The minor diameter of the external thread—whether cannulized or not—is, for example, selected from a value range between 3.5 mm and 7 mm, in particular between 4 mm and 6 mm. It in particular at least amounts to approximately 5 mm. A good handling capability of the screw, a good fitting capability in the with a small weakening of the bone material and a sufficiently large strength of the screw bones result with these dimensions.

It has proved to be advantageous if that second axial section in which the outside diameter of the external thread increases as the spacing from the front end increases has a conical enveloping contour with an opening angle which in particular amounts to between 5° and 6° as a full cone angle.

Particularly good results for achieving a friction-induced fixing function with a simultaneous avoidance of compression are achieved in accordance with a further development if an outer diameter ratio of a maximum outer diameter of the second axial section with the constant outer diameter of the first axial section is selected from a value range between 1.0 and 1.4, in particular between 1.1 and 1.3. The ratio in particular amounts to at least approximately 1.2. A good friction-induced inhibition of the thread turns results in the end position of the implanted screw with these ratios.

The maximum outer diameter of the second axial diameter can in particular also correspond to the maximum outer diameter of the external thread overall. The maximum outer diameter of the second axial section in particular represents the maximum diameter of the screw overall, i.e. the screw does not comprise any part or section, in particular no head, whose largest diameter is larger than the maximum outer diameter of the second axial section. The screw can in particular be called a "grub screw" in this respect. The screw accordingly does not have any shape-matched mechanical abutment which would fixedly bound the screw-in depth of the screw.

The outer diameter of the external thread in the first axial section is selected from a value range between 5.5 mm and 10 mm, in particular between 6 mm and 8 mm and in particular amounts at least approximately to 7.5 mm. The maximum outer diameter of the external thread in the second axial section is in particular selected from a value range between 7 mm and 12 mm, in particular between 8 mm and 11 mm, and amounts at least approximately to 9 mm, for example. A good handling capability of the screw, a good fitting capability in the bones with a small weakening of the bone material, a sufficiently large strength of the screw as well as a good friction-induced inhibition of the thread turns in the end position of the implanted screw result with these dimensions.

It also has a positive effect on the locking function or on the ensuring of a defined introduction position if the length ratio of the total length of the locking screw to the length of the second axial section, in particular having a conical enveloping contour, is selected from a value range between 2.5 and 5.0, in particular between 3.0 and 4.5.

It is particularly expedient in this respect if the total length of the locking screw is selected from a value range between 50 mm and 100 mm, in particular between 60 mm and 90 mm, and in particular amounts to 65 mm, 70 mm, 75 mm, 80 mm or 85 mm. The length of the second axial section is selected, for example, from a value range between 10 mm and 30 mm and in particular amounts at least approximately to 20 mm. The selection of these geometrical parameters can further assist the function of the screw in an embodiment.

In an embodiment of the locking screw, a further external thread section is arranged at the axially rear, proximal end of the screw, the further external thread section extending, for example, over one to two thread turns and having a reduced external thread diameter with respect to the largest diameter of the second axial section, with the external thread diameter in particular reducing in the direction of the rear, proximal end of the screw. This tapering ensures the minimization of any overhang or an improved adaptation to anatomical circumstances, whereby the healing success is improved. The second axial section can naturally also extend up to the axial rear, proximal end of the screw in an embodiment.

To ensure a secure hold of the locking screw, provision can be made that the locking screw is formed as a self-tapping screw so that a maximum of one minor diameter bore has to be prebored and the external thread of the locking screw screws independently into the tissue or into the bone. For this purpose, cutting means are provided in accordance with a further development which are in particular attached to the front end of the screw, with the cutting means being able at least to comprise a recess which extends from radial outside to radial inside and which interrupts a thread turn.

In a further embodiment of the locking screw, an axial front, distal end face is configured as a cutter head. One or more, for example three, radially extending or radially running blades, which in particular act axially forwardly, are arranged, for example, at the distal end face of the screw. This makes it possible to configure the screw as self-drilling such that it can be inserted directly, i.e. without preboring. A cannulized screw can in this respect be implanted directly via a Kirschner wire acting as a guide.

The rear, proximal end face of the screw is provided in an embodiment with a drive and/or with an appendage for a tool, for example with a hexagon socket or a Torx drive.

The external thread can have at least one multi-turn section having two or more than two thread turns, with in particular each thread turn of the multi-turn section per se having a constant thread pitch. The multi-turn section can furthermore extend over at least a region of the axial extent of the external thread, i.e. the external thread does not necessarily have to be multi-turn over its total axial length. In this respect, each thread turn of the multi-turn section can have a constant thread pitch.

In summary, the locking screw described here is characterized inter alia by the following properties: Unwanted additional compression on the fracture gap is avoided by the cylindrical core and by the constant thread pitch. The distal thread section having a constant diameter which in particular extends over a large part of the length of the locking screw allows a simple implanting since the thread only has to be cut in the region of the axial frontmost, distal thread turn, whereas the remainder of this thread slides through the pre-cut thread turns with a constant outer diameter. The section with the outer thread diameter increasing in size from distal to proximal moves into engagement with the bone toward the end of the implanting phase. This thread section has to constantly cut in again with a further axial feed. The thread tips of this section are thereby always in freshly displaced bone material on the ending of the screw-in process and are therefore acted on by a large friction force. The resulting friction torque effects a secure locking of the screw in the bone.

The following can be provided in exemplary embodiments: A cannulization allows the guided implanting via a Kirschner wire. A cutter head at the front, distal end face allows the implanting without preboring. Self-tapping threads allow the implanting without precutting threads in the bone. A drive at the rear, proximal end face allows a comfortable handling of the implant. The suitable choice of specific geometrical parameters further improves the function of the locking screw.

The above-named features can naturally be combined with one another. Further advantages, features and details of the invention result from the following description of embodiments and with reference to the drawing.

Figure 2:
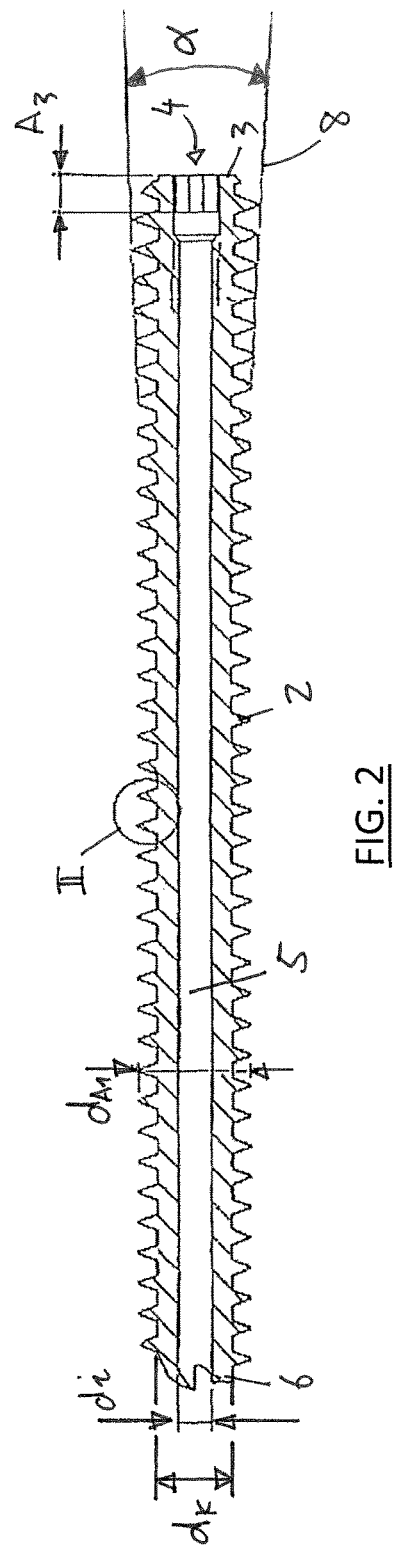
Figure 3:
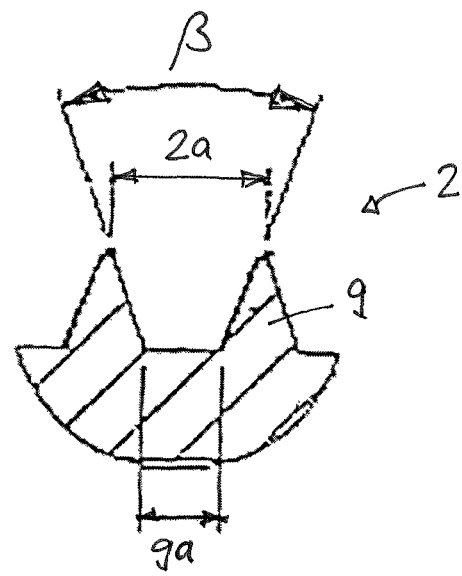
Figure 4:
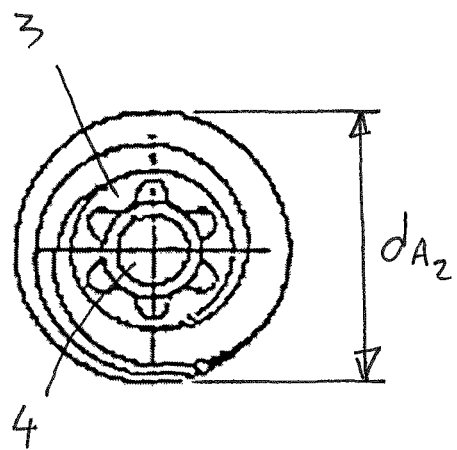

They show in:

FIG. 1: a side view of a locking screw configured in accordance with the concept of the invention;

FIG. 2: a longitudinal sectional view of the locking screw in accordance with FIG. 1;

FIG. 3: a detail of the external thread of the locking screw in a first axial section;

FIG. 4: a view of the locking screw from the front; and

Figure 5:
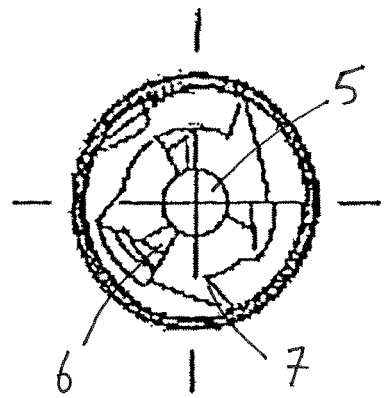

FIG. 5: a view of the locking screw from behind.

A surgical locking screw 1 formed from metal, for example from a titanium alloy, for fixing bone pieces in the case of a heel fracture is shown in FIG. 1. The locking screw 1 does not have a compression function, but rather an axially throughgoing external thread 2, here a single-turn thread, having an axially continuously, invariable minor diameter $d_K$. The screw can generally also comprise and/or consist of suitable non-metallic materials.

The locking screw 1 can be divided into a first axial section $A_1$ and into a second axial section $A_2$. The outer diameter of the external thread does not change in the first axial section $A_1$ which constantly has the external thread 2. The outer diameter dm (FIG. 2) is therefore constant over the longitudinal extent of the first axial section $A_1$ and amounts to 7.5 mm in the embodiment shown.

In contrast, an outer diameter $d_{A2}$ of the external thread 2 in the second axial section $A_2$ is not constant, but rather increases with a conical enveloping contour 8. Starting from a transition between the first and the second axial sections $A_1, A_2$, the conical enveloping contour 8 opens at an opening angle α in the direction of a rear end 3 of the locking screw 1 up to a maximum outer diameter $d_{A2}$ of the second axial section $A_2$ which simultaneously corresponds to the maximum outer diameter of the external thread 2 and to the maximum diameter of the screw 1 overall (FIG. 4). In the embodiment shown, the opening angle α amounts to between 5° and 6° and the maximum outer diameter $d_{A2}$ amounts to 9 mm.

Since the locking screw 1 has an axially continually invariable minor diameter $d_K$ and simultaneously has a rearwardly increasing outer diameter of the external thread 2 in the second axial section $A_2$, a secure positioning of the locking screw 1 in the human heel is made possible without any compression of the bone parts occurring.

The rear, proximal end 3 of the locking screw 1 is formed by an outer diameter section $A_3$ which adjoins the second axial section $A_2$, which is comparatively short and which extends over approximately 1.5 thread turns in which the external thread diameter of the external thread 2 reduces again toward the rear.

FIG. 3 shows an enlarged view of the region II in accordance with FIG. 2 in which a section of the external thread 2 having two adjacent thread sections of the thread turn 9 can be recognized which has a thread pitch 2a which is constant over the axial length of the locking screw 1. The external thread furthermore has a flank angle β which amounts to 40° in the embodiment. The thread sections 9 are spaced apart from one another in the manner of a trapezoidal thread having a spacing 9a and have a triangular profile.

A drive 4 formed as a Torx drive is introduced in the rear end 3 of the locking screw 1 (FIG. 4).

As in particular results from FIG. 2, the locking screw 1 is provided with an axially throughgoing cannulization 5 having an inner diameter $d_i$ of 2.2 mm in the embodiment shown for receiving a Kirschner wire.

In the region of a front end 6 of the locking screw 1 remote from the drive 4, the locking screw is provided with cutting means 7 in the form of indentations in order thus to obtain a self-tapping and self-drilling locking screw. The cutting means 7 comprise three notches (FIG. 5) which reach up to the axially front end 6 and which in so doing interrupt windings of the external thread 2. Three radially extending and axially acting cutting edges are arranged at the distal end face of the screw. In the embodiment shown, an axial length of the cutting means 7 amounts to 3 mm.

The cutting means 7 allow an introduction into the bone without it being necessary previously to cut a counter-thread therein, whereby an ideal thread fit and thus a secure hold of the locking screw 1 is ensured.

REFERENCE NUMERALS 1 locking screw
2 external thread
2a thread pitch
3 rear end
4 drive
5 cannulization
6 front end
7 cutting means
8 enveloping contour
9 thread turn
9a spacing
$A_1$ first axial section
$A_2$ second axial section
$A_3$ rear external thread section
$d_{A1}$ outer diameter in the first axial section
$d_{A2}$ outer diameter in the second axial section
$d_i$ inner diameter of the cannulization
$d_K$ minor diameter

The invention claimed is:

1. A surgical locking screw for fixing bone parts in the case of a heel fracture, the locking screw comprising a front end, having a rear drive end comprising a drive for rotating the locking screw and having an external thread which has an invariable thread pitch over its axial extent in a throughgoing manner, wherein an outer diameter of the external thread is constant in a first axial section of the locking screw and increases in a second axial section adjacent to the first axial section in the direction of the rear end as the spacing from the front end increases, wherein a minor diameter of the external thread is constant in the first and second axial sections, wherein the external thread extends at least approximately in an axially throughgoing manner over the total axial extent of the locking screw, wherein the minor diameter of the external thread extends over the total axial extent of the external thread, and wherein a third external thread section, which extends over one to two thread turns and which has a reduced external thread diameter with respect to the largest external diameter of the second axial section is provided axially rearwardly adjoining the second axial section.

2. The locking screw in accordance with claim 1, wherein the locking screw has an axially throughgoing central cannulization for receiving a Kirschner wire.

3. The locking screw in accordance with claim 1, wherein the second axial section has a conical enveloping contour.

4. The locking screw in accordance with claim 1, wherein an outer diameter ratio of a maximum outer diameter of the second axial section to the constant outer diameter of the first axial section is selected from a value range between 1.05 and 1.4.

5. The locking screw in accordance with claim 1, wherein a length ratio of the total length of the locking screw to the length of the second axial section is selected from a value range between 2.5 and 5.0.

6. The locking screw in accordance with claim 1, wherein the length of the second axial section is selected from a value range between 10 mm and 30 mm.

7. The locking screw in accordance with claim 1, wherein the locking screw is configured as a self-tapping screw having cutting means which are arranged at the front end.

8. The locking screw in accordance with claim 1, wherein the external thread has at least one multi-turn section having two or more than two thread turns and extending at least over a region of the external extent of the external thread.

9. The locking screw in accordance with claim 8, wherein the plurality of thread turns of the multi-turn section each have a constant thread pitch.

10. The locking screw in accordance with claim 1, wherein a maximum outer diameter of the second axial section corresponds to the maximum outer diameter of the external thread.

11. The locking screw in accordance with claim 1, wherein the external thread comprises a flank angle, which is between 35° and 45°, at least over a region of the axial extent.

12. The locking screw in accordance with claim 1, wherein the external thread is configured as trapezoidal at least over a region of the axial extent.

13. A surgical locking screw for fixing bone parts in the case of a heel fracture, the locking screw comprising a front end, having a rear drive end comprising a drive for rotating the locking screw and having an external thread which has an invariable thread pitch over its axial extent in a throughgoing manner, wherein an outer diameter of the external thread is constant in a first axial section of the locking screw and increases in a second axial section adjacent to the first axial section in the direction of the rear end as the spacing from the front end increases to define a conical enveloping contour, wherein a minor diameter of the external thread is constant in the first and second axial sections, wherein the external thread extends at least approximately in an axially throughgoing manner over the total axial extent of the locking screw, wherein the minor diameter of the external thread extends over the total axial extent of the external thread, wherein a third external thread section, which has a reduced external thread diameter with respect to the largest external diameter of the second axial section is provided axially rearwardly adjoining the second axial section, and wherein the external thread is configured as trapezoidal at least over a region of the axial extent.

14. The locking screw in accordance with claim 13, wherein a maximum outer diameter of the second axial section corresponds to the maximum outer diameter of the external thread.

15. The locking screw in accordance with claim 14, wherein the locking screw has an axially throughgoing central cannulization.

16. The locking screw in accordance with claim 15, wherein a length ratio of the total length of the locking screw to the length of the second axial section is selected from a value range between 2.5 and 5.0.

17. The locking screw in accordance with claim 15, wherein an outer diameter ratio of a maximum outer diameter of the second axial section to the constant outer diameter of the first axial section is selected from a value range between 1.05 and 1.4.

\* \* \* \* \*